US00PP25967P3

(12) United States Plant Patent
Duncalf

(10) Patent No.: US PP25,967 P3
(45) Date of Patent: Sep. 29, 2015

(54) ***AGAPANTHUS* PLANT NAMED 'DUNAGA02'**

(50) Latin Name: ***Agapanthus* hybrid**
Varietal Denomination: DUNAGA02

(71) Applicant: Ian Duncalf, Tauranga (NZ)

(72) Inventor: Ian Duncalf, Tauranga (NZ)

( * ) Notice: Subject to any disclaimer, the term of this patent is extended or adjusted under 35 U.S.C. 154(b) by 186 days.

(21) Appl. No.: 13/986,997

(22) Filed: Jun. 21, 2013

(65) Prior Publication Data

US 2014/0380541 P1 Dec. 25, 2014

(51) Int. Cl.
*A01H 5/02* (2006.01)

(52) U.S. Cl.
USPC ..... Plt./398

(58) Field of Classification Search
USPC ..... Plt./398
CPC ..... A01H 5/02; A01H 5/0272; A01H 5/025
See application file for complete search history.

(56) References Cited

PUBLICATIONS

Dawson et al. *Agapanthus* in New Zealand. New Zealand Garden Journal, Jun. 2012, vol. 15(1), pp. 2-18.*
Growing Spectrum Full Plant Catalogue 2012, retrieved on Feb. 4, 2015, retrieved from the Internet at <www.growingspectrum.co.nz> pp. 1-4 and 9.*
Anthony Tesselaar International 2012. Thunder Storm *Agapanthus,* retrieved on Feb. 4, 2015, retrieved from the Internet at <www.tesselaar.com/plants/storm-agapanthus/thunder-storm/> 3 pp.*

* cited by examiner

*Primary Examiner* — June Hwu
(74) *Attorney, Agent, or Firm* — Cassandra Bright

(57) ABSTRACT

A new and distinct *Agapanthus* cultivar named 'DUNAGA02' is disclosed, characterized by reliable flowering, variegated leaves and small growth form. The new variety is tolerant of glyphosate and sterile. The new variety is a *Agapanthus*, typically produced as an outdoor ornamental plant.

3 Drawing Sheets

Latin name of the genus and species: *Agapanthus* hybrid.
Variety denomination: 'DUNAGA02'.

BACKGROUND OF THE INVENTION

The new cultivar is the product of chance discovery. The new variety originated as a naturally occurring mutation of the unpatented 'Gayles Lilac' variety of *Agapanthus*.

The new variety was discovered by the inventor, Ian Duncalf, a citizen of New Zealand, during 1997 in an outdoor planting of nursery pots, in a commercial nursery in Tauranga, New Zealand. After identifying the new variety as a potentially interesting selection, the inventor continued confidential testing and observation of 'DUNAGA02' until around 2002, finally selecting the variety for further propagation during 2004.

Asexual reproduction of the new cultivar 'DUNAGA02' was first performed by division in Tauranga, New Zealand, during 2002, on a very limited basis. Access to all plants was restricted, as plants were kept in a location not open to the public. Through subsequent propagation, multiple generations have been reproduced, which have shown that the unique features of this cultivar are stable and reproduced true to type.

SUMMARY OF THE INVENTION

The cultivar 'DUNAGA02' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DUNAGA02.' These characteristics in combination distinguish 'DUNAGA02' as a new and distinct *Agapanthus* cultivar:

1. Variegated foliage.
2. Reliable late season flowering.
3. Sterile non seed producing plants.
4. Glyphosate tolerant.
5. Attractive small plant size and controlled growth habit.
6. Lilac-blue flowers.

PARENT COMPARISON

Plants of the new cultivar 'DUNAGA02' are similar to the parent, *Agapanthus* 'Gayles Lilac' in most horticultural characteristics. The new variety, however, produces variegated foliage, compared to the solid colored foliage of parent 'Gayles Lilac'. Additionally, plants of 'DUNAGA02' are smaller than plants of the parent variety. Plants of 'DUNAGA02' are approximately two thirds the size of parent 'Gayles Lilac'.

COMMERCIAL COMPARISON

Plants of the new cultivar 'DUNAGA02' are similar to the commercial variety *Agapanthus* 'Tinkerbell' in most horticultural characteristics. The new variety, however, produces yellow-green variegated leaves whereas 'Tinkerbell' produces silver-green variegated leaves. 'DUNAGA02' also consistently produces flowers regularly whereas 'Tinkerbell' flowers infrequently and erratically. The consistent flowering of 'DUNAGA02' makes plants much more suitable for commercial production.

BRIEF DESCRIPTION OF THE PHOTOGRAPHS

The accompanying photograph in FIG. 1 illustrates in full color a typical foliage of 'DUNAGA02' grown in Tauranga, New Zealand.

Figure 1:
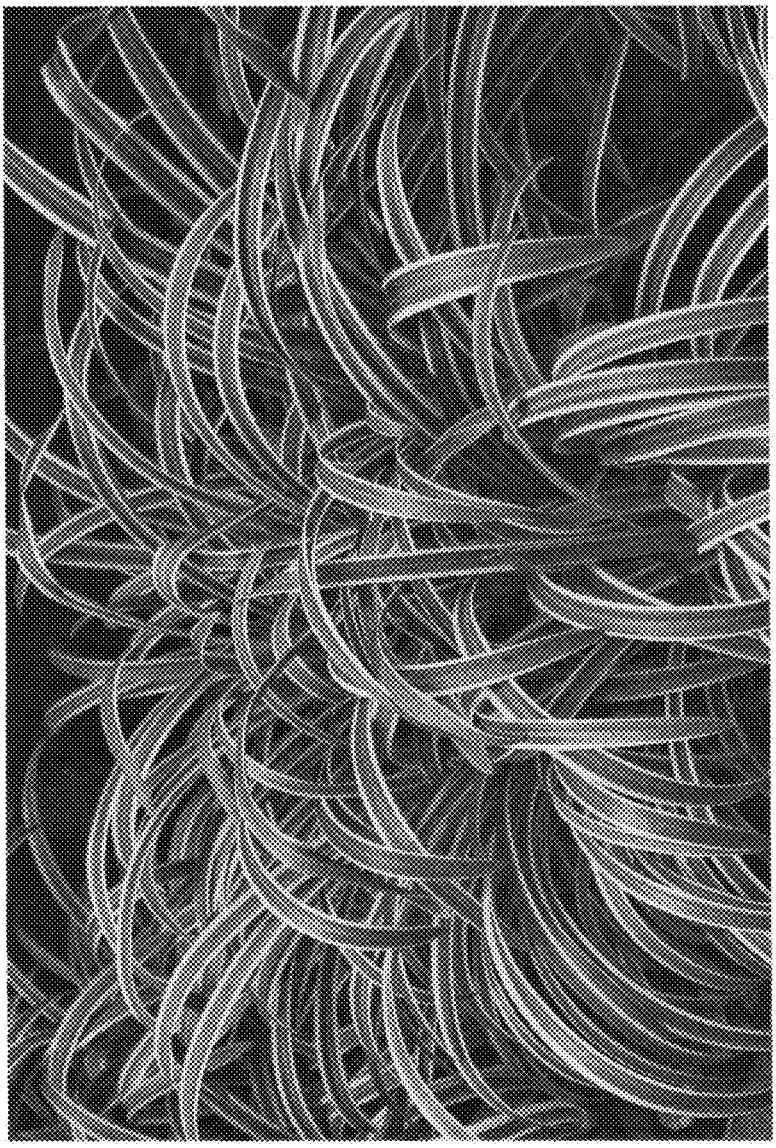
Figure 2:
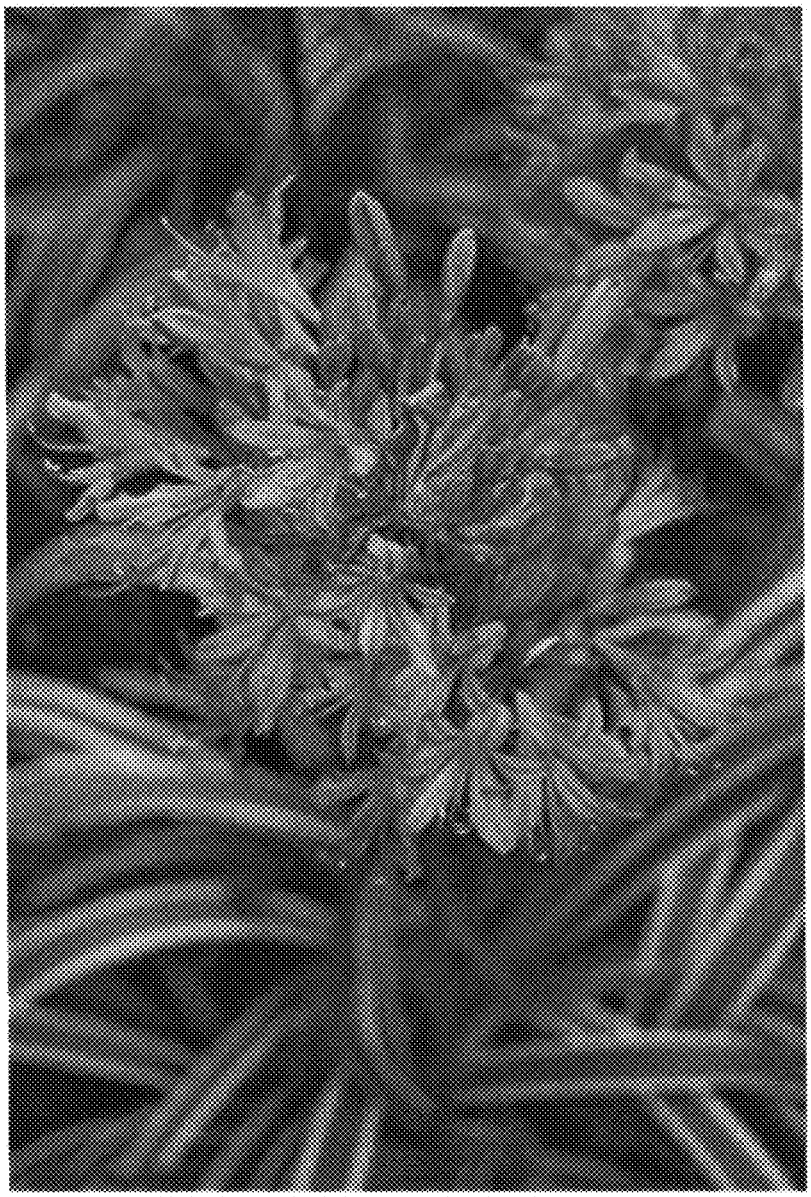
FIG. 2 illustrates in full color a close up of the flowers of 'DUNAGA02.
Figure 3:
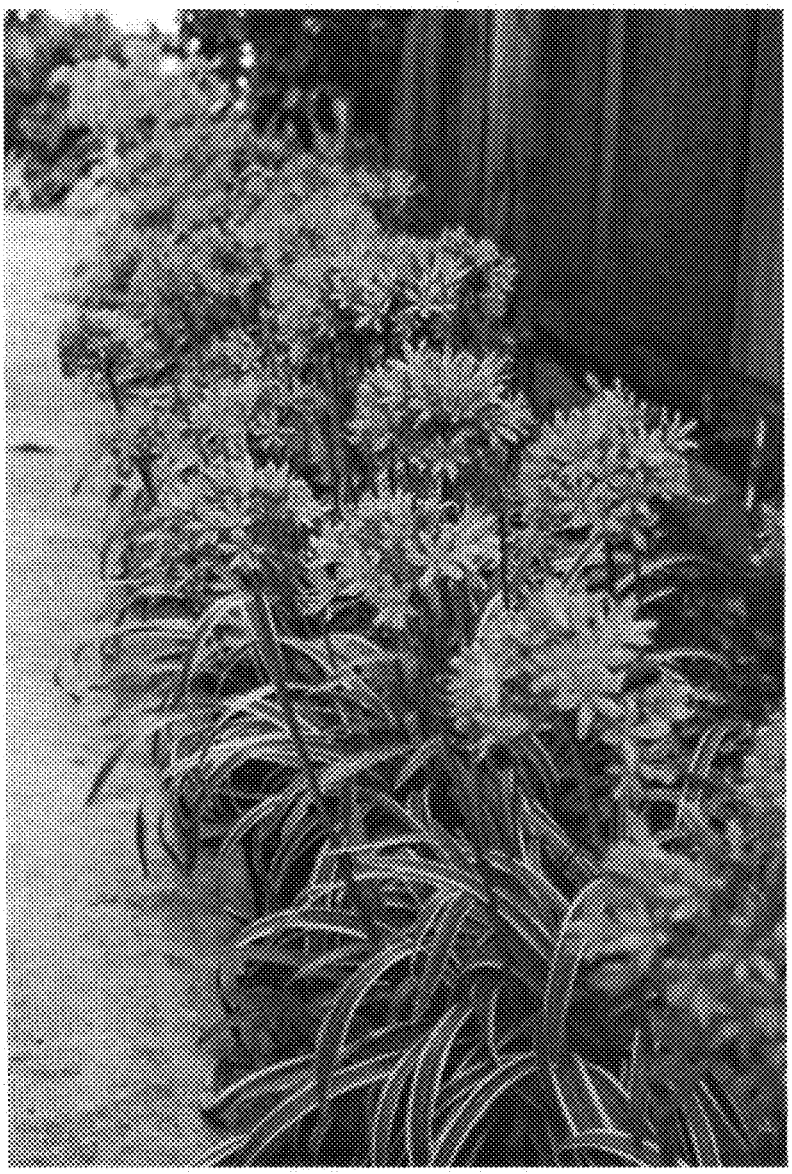
FIG. 3 illustrates mature plants grown in the ground.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'DUNAGA02' plants grown outdoors in Tauranga, New Zealand. Plants are approximately 1 year old. Temperatures ranged from approximately 8° C. to 15° C. at night and 10° C. to 32° C. during the day. No artificial light, photoperiodic treatments were given to the plants. No chemical treatments were given to plants. Measurements and numerical values represent averages of typical plant types.

Botanical classification: *Agapanthus* hybrid 'DUNAGA02'.

PROPAGATION

Root description: Thick, fleshy root system colored near Brown 199D and N199B.

PLANT

Growth habit: Clump forming tender perennial with arching, pendulous foliage. Plants evergreen to −5° F.

Height: Foliar plane 400 to 500 mm. Flowering plane up to 600 mm.

Plant spread: Approximately 400 to 500 mm.

Growth rate: Moderate, slower growth than non-variegated forms.

Diameter of stem: Flower stems 8 to 10 mm.

Growth pattern: The plant makes growth throughout most of the year but particularly in the summer months. This grow is in the form of basal shoots or pups as well as some leaf extension. From mid summer flowers start to appear and remain for much of the summer.

FOLIAGE

Leaf:

*Average leaf length.*—Approximately 260 to 290 mm.

*Average leaf width.*—Approximately 15 to 19 mm.

*Color.*—Leaf color is influenced by the amount of sun exposure. Information below relates to plants in full sun.

*Coloration for both upper and lower surfaces.*—Leaf Margin: Near Yellow group RHS 6A through 4D, all shades of yellow present. Leaf center: Near Green group RHS Yellow-Green 144A.

FLOWER

Natural flowering season: Late season, starts in mid summer.

Length of flowering period: Approximately 8 weeks.

Inflorescence type: Terminal Umbel with approximately 48 individual flowers.

Individual flower type: Single.

Flower profile: Funnelform.

Lasting quality: Inflorescence shows no significant signs of aging for approximately 6 to 7 weeks.

Bud:

*Shape.*—Ovate.

*Color.*—Near Blue group RHS 102C.

Flower head size:

*Diameter.*—100 to 120 mm.

*Stem length.*—300 to 400 mm.

Individual flowers:

*Length.*—Average 2.8 cm.

*Width.*—Average 2.4 cm.

Tepals:

*Arrangement.*—Rotate, not touching or overlapping when open.

*Length.*—Average 20 mm.

*Width.*—Average 4 to 8 mm.

*Quantity.*—6.

*Tepal lobe.*—Length: Average 1.7 cm. Width: Average 0.4 cm. Shape: Linear. Margin: Entire. Base: Fused. Apex: Varies, acute or occasionally mucronate.

*Perianth tube.*—Length: Color: Inner surface: Near Violet-Blue 91D. Outer surface: Near Violet-Blue 91B.

Flower color upper and lower surfaces: Near Violet-blue group RHS 94D. Center line stripe of coloration near Violet-Blue 94A lower surface, near Violet-Blue 93A upper surface.

Flower filament color: Near Violet-Blue group RHS 94C.

Flower anther color: Near Greyed-Yellow group RHS 160D.

Anther quantity: 6, each approximately 0.2 cm long.

Stamen protrusion: Protrudes slightly past the floral lobe apex.

Pistil:

*Number.*—1.

*Length.*—Approximately 2.5 cm.

*Stigma.*—Shape: Linear. Color: Near RHS Violet-Blue 94D.

Flower style color: Near Violet-Blue group RHS 94C.

Pedicel:

*Length.*—20 mm.

*Texture.*—Glabrous.

*Color.*—Near Green 143C.

Fragrance: None.

OTHER CHARACTERISTICS

Seed production: Sterile, no seed produced to date.

Disease resistance: Seems unaffected by any disease.

Temperature tolerance: Not tested but expected to handle −5° C. to +30° C.

Drought tolerance: Will tolerate considerable dryness once established.

What is claimed is:

1. A new and distinct cultivar of *Agapanthus* plant named 'DUNAGA02' as herein illustrated and described.

* * * * *